United States Patent [19]
Herkes

[11] Patent Number: 5,808,078
[45] Date of Patent: Sep. 15, 1998

[54] PROCESS FOR PREPARATION OF 1-ALKYL-3-METHYLPIPERIDONE-2 AND 1-ALKYL-5-METHYLPIPERIDONE-2

[75] Inventor: Frank Edward Herkes, Wilmington, Del.

[73] Assignee: E. I. duPont de Nemours and Company, Wilmington, Del.

[21] Appl. No.: 853,182

[22] Filed: May 8, 1997

Related U.S. Application Data

[63] Continuation-in-part of Ser. No. 708,999, Feb. 7, 1997, abandoned.

[51] Int. Cl.$^6$ ................................................. C07D 211/36
[52] U.S. Cl. ............................................................ 546/243
[58] Field of Search ...................................... 546/290, 243

[56] References Cited

U.S. PATENT DOCUMENTS

| | | | |
|---|---|---|---|
| 3,095,423 | 6/1963 | Copenhaver | 548/553 |
| 3,673,251 | 6/1972 | Frampton et al. | 564/469 |
| 3,781,298 | 12/1973 | Davis | 548/553 |
| 3,966,763 | 6/1976 | Greene | 548/553 |
| 4,042,599 | 8/1977 | Greene | 548/553 |
| 4,152,331 | 5/1979 | Meijer et al. | 548/553 |
| 5,449,780 | 9/1995 | Kosak | 546/243 |

*Primary Examiner*—Ceila Chang
*Assistant Examiner*—Garth M. Dahlen

[57] ABSTRACT

This invention relates to an improved process for the preparation of 1-alkyl-3-methylpiperidone-2 and 1-alkyl-5-methylpiperidone-2 from 2-methylglutaronitrile wherein the selectivity of the process to bis-1,5-(methylamido)-3-methylpentane is less than 8%.

6 Claims, 2 Drawing Sheets

PROCESS FOR PREPARATION OF 1-ALKYL-3-METHYLPIPERIDONE-2 AND 1-ALKYL-5-METHYLPIPERIDONE-2

This is a continuation-in-part of application Ser. No. 08/708,999, filed Sep. 6, 1996, now abandoned.

This invention relates to an improved process for the preparation of 1-alkyl-3-methylpiperidone-2 and 1-alkyl-5-methylpiperidone-2 from 2-methylglutaronitrile.

BACKGROUND OF THE INVENTION

2-Methylglutaronitrile is a by product in the hydrocyanation of butadiene to form adiponitrile. The adiponitrile has many uses including hydrogenation to hexamethyene diamine, which is one of the components of nylon 6,6. 2-Methylglutaronitrile has few industrial uses, but it has been shown that 2-methylglutaronitrile may be converted by a batch process into 1-alkyl-3-methylpiperidone-2 and 1-alkyl-5-methylpiperidone-2 by reaction of the 2-methylglutaronitrile, a primary alkylamine having from 1 to 18 carbon atoms, water and hydrogen in the presence of a hydrogenation catalyst. 1-Alkyl-3-methylpiperidone-2 and 1-alkyl-5-methylpiperidone-2 are useful as solvents; each having solvent properties similar to other N-alkyl lactams.

The batch process for conversion of 2-methylglutaronitrile into 1,3 and 1,5-dialkylpiperidone-2 was taught by Kosak in U.S. Pat. No. 5,449,780. This process starts as a two phase reaction mixture, but becomes a single phase as all the hydrogen is reacted. The Kosak process is also known to have a high selectivity, 12 to 40%, to bis-1,5-(alkylamido)-3-methylpentane and to also include concentrations of other undesirable high boilers. The presence of bis-1,5-(alkylamido)-3-methylpentane is a problem in the refining of product alkylmethlypiperidone-2, and its presence is particularly a problem in the refining of dimethylpiperidone-2 since the bis-1,5-(methylamido)-3-methylpentane is thermally cyclized during the distillation process to form 1,3-dimethylglutarimide. The formation of 1,3-dimethylglutarimide not only effects the operation of the vacuum distillation by the evolution of the methylamine, but it is co-distilled with the product dimethylylpiperidone-2 making it virtually impossible to easily produce a dimethylpiperidone-2 pure product stream. In the case of higher alkylmethylpiperidone-2's than the dimethylpiperidone-2, the corresponding bis-1,5-(alkylamido)-3-methyl-pentane from the synthesis reaction will form the corresponding 1-alkyl-3-methylglutarimide during distillation and cause the evolution of the corresponding volatile alkylamine.

SUMMARY OF THE INVENTION

The continuous process of the present invention is a process for the preparation of 1-alkyl-3-methylpiperidone-2 and 1-alkyl-5-methylpiperidone-2 from hydrogen and a single phase, liquid reaction mixture of 2-methylglutaronitrile, a water solution of a primary alkylamine which contains from 1 to 18 carbons, a homogenizing solvent in the presence of a hydrogenation catalyst comprising the steps of:

(a) contacting the hydrogenation catalyst in a reaction vessel with the single phase liquid reaction mixture wherein the weight percents of the homogenizing solvent, the water solution of the primary alkylamine, and 2-methylglutaronitrile based on the total weight of the single phase liquid reaction mixture are within the region of FIG. 1 bounded by the lines AB, BC, and AC;

(b) feeding into the reaction vessel one or more reactant streams containing 2-methylglutaronitrile, the water solution of the alkylamine and hydrogen;

(c) heating the reaction mixture to a temperature above about 150° C. at a hydrogen pressure above about 27 bars (400 psi); and (d) withdrawing a product stream from the reaction mixture containing 1,3- and 1,5-alkyl-methylpiperidone-2 while at the same time continuing to feed into the reaction vessel the reactant streams of step (b) in such a way as to maintain the weight percent of the homogenizing solvent, the water solution of the alkylamine, and 2-methylglutaronitrile based on the total weight of the single phase liquid reaction mixture within the region of FIG. 1 bounded by the lines AB, BC, and AC. The present process has selectivity less than 8% to the formation of bis-1,5-(alkylamido)-3-methylpentane.

The homogenizing solvent may be any solvent, non-reactive in the reaction environment, which is miscible with water and in which the alkylamine and 2-methylglutaronitrile are soluble to the limits required in FIG. 1.

The process of the present invention may also be run as a batch process.

As a batch process run at a pressure of above about 27 bars (400 psi) and a temperature of above about 150° C., the process of the present invention provides improved selectivity to the products l-alkyl-3-methylpiperidone-2 and 1-alkyl-5-methylpiperidone-2. The improvement of the present process comprises mixing with the hydrogenation catalyst, a single phase liquid mixture of 2-methylglutaronitrile, the water solution of the primary alkylamine and a homogenizing solvent such that the concentrations of each of these components as weight percents of the total liquid phase fall within the region of FIG. 1 bounded by the lines AB, BC and AC.

The preferred primary alkylamine for this process is methylamine, and the preferred products are 1,3-dimethylpiperidone-2 and 1,5-dimethylpiperidone-2.

DETAILED DESCRIPTION

As used herein the term selectivity means the weight of the particular product divided by the total weight all products in the product stream.

U.S. Pat. No. 5,449,780 to Kosak (Kosak) taught a batch process for hydrogenating 2-methylglutaronitrile to 1,3 and 1,5-dialkylpiperidone-2. In the process of this patent, a mixture of the reactants, 2-methylglutaronitrile, water, an alkylamine and a hydrogenation catalyst, is charged into a reactor. The reactor is then purged and pressurized with hydrogen, and heated to the proper conditions for reaction.

It is known that under the reaction conditions of Kosak that the liquid reactants, as well as the dissolved byproduct ammonia, remain in substantially two separate phases throughout the majority reaction process. The 2-methylglutaronitrile has only limited solubility in the aqueous amine solution and the concentration of the amine is predominately distributed in the water phase. Thus, in the Kosak reaction system, there are present the solid catalyst phase, the gas phase and two liquid phases. The Kosak process also has a high selectivity to the formation of high boiler byproducts, particularly towards the formation of bis-1,5-(alkylamido)-3-methylpentane. In the reaction of methylamine with 2-methylglutaronitrile, the selectivity of the Kosak process to bis-1,5-(methylamido)-3-methylpentane ranges from 12 to 40%. During the refining process, this byproduct (and when the synthesis is carried out with amines higher than methylamine, corresponding higher alkyl byproducts of this analogous structure) causes serious problems in producing a purified product. Under the distillation conditions the byproduct bis-1,5-(methylamido)-3-methylpentane (and corresponding higher alkyl compounds formed in the synthesis of the 1-alkyl-3-methylpiperdone-2 or 1-alkyl-5-methylpiperdone-2 according to Kosak) is cyclized according to the reaction shown below:

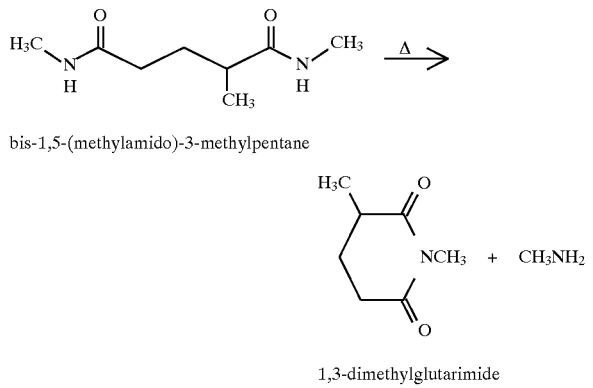

bis-1,5-(methylamido)-3-methylpentane 1,3-dimethylglutarimide

Figure 1:
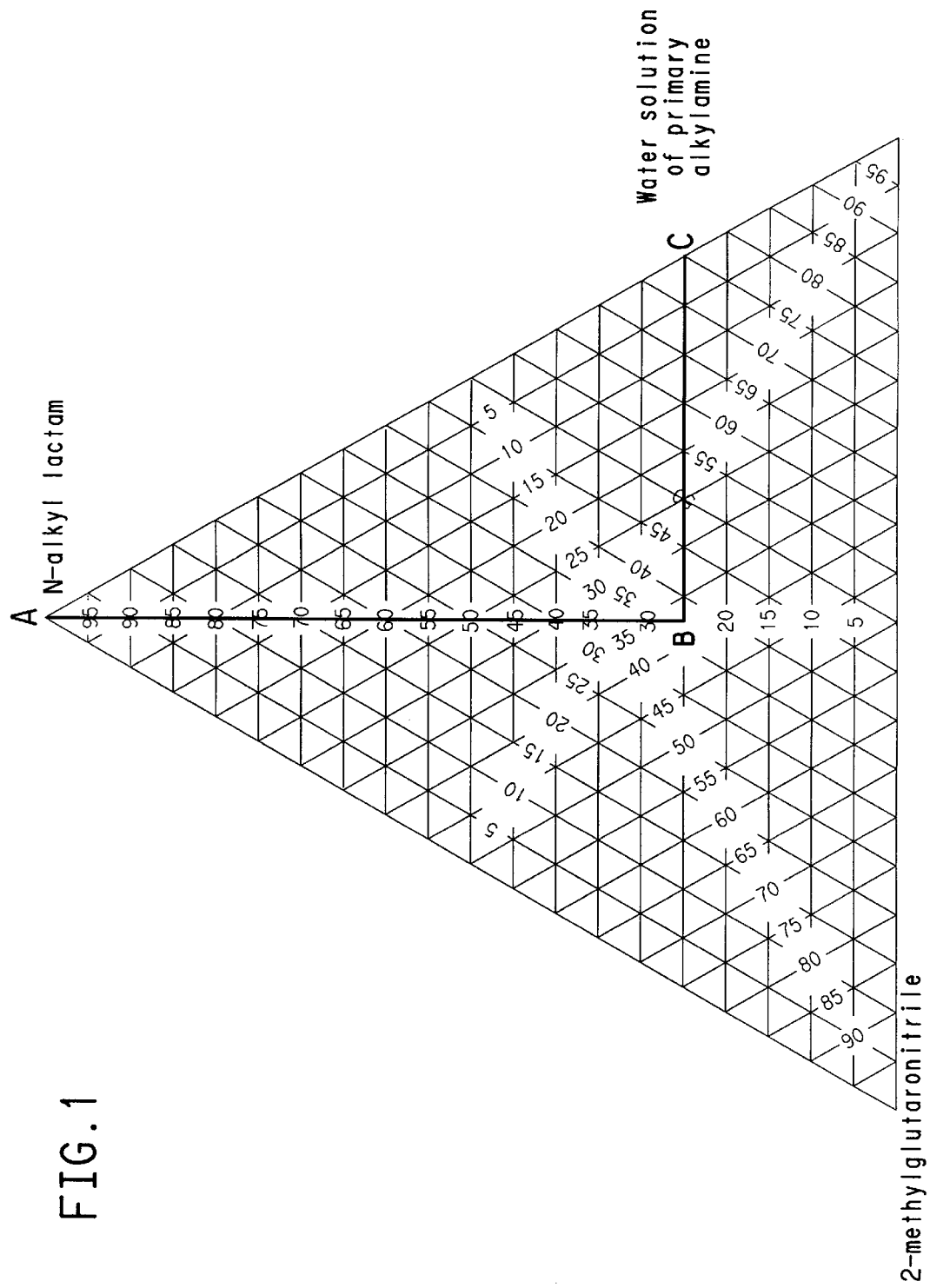
FIG. 1 shows, the region of the single, phase liquid reaction mixture, that is the region bounded by the lines AB, BC and AC, and the concentrations of 2-methylglutaronitrile, the water solution of the primary alkylamine and the homogenizing solvent according to the present invention as weight percents of the total weight of the single, liquid phase of the reaction mixture.

In the continuous, single liquid phase process of the present invention, the continuous removal of product combined with the continuous feed of the reactants, according to FIG. 1, allows the reaction to take place in one single liquid phase and results in a low selectivity towards high boiling by products, particularly bis-1,5-(alkylamido)-3-methylpentane. This single phase reaction seems to be more favorable with respect to equilibrium and kinetic considerations than the teachings of the prior art.

The single liquid phase reaction of the present invention is achieved by the addition of a homogenizing solvent to the mixture of the reactants and the catalyst. Throughout the reaction, the present process continues to maintain the concentrations of the water solution of the alkylamine, the homogenizing solvent, and 2-methylglutaronitrile (as weight percents of the total weight of the liquid phase reaction mixture) within the single phase region—that is that region bounded by the lines connecting points A, B, and C of FIG. 1.

The homogenizing solvent may be any solvent, non-reactive in the reaction environment, which is miscible with water and in which the alkylamine and 2-methylglutaronitrile are soluble to the limits required in FIG. 1. Preferred solvents are dioxane, N-methylpyrrolidone, 1-alkyl-3-methylpiperidone-2 or 1-alkyl-5-methylpiperidone-2or a mixture of 1-alkyl-3-methylpiperidone-2 and 1-alkyl-5-methylpiperidone-2 or other N-methyl or higher N-alkyl lactams that posses the required properties of water miscibility and solubility for the alkylamine and 2-methylglutaronitrile. In particular, a mixture of 1,3 and 1,5-dimethylpiperidone-2, or N-methylpyrrolidone is preferred as the homogenizing solvent.

In the present process a homogenizing solvent in which the product 1-alkyl-3-methylpiperidone-2 and 1-alkyl-5-methylpiperidone-2 is soluble is preferred, but not required so long as the product 1-alkyl-3-methylpiperidone-2 and 1-alkyl-5-methylpiperidone-2 can be drawn off as a continuous, homogeneous product stream.

In the continuous process, the concentration limits of FIG. 1 may be met by adjusting the ratios of the reactant feed (the water solution of the alkylamine and 2-methylglutaronitrile) and the product take-off to be within the region of a single phase mixture as defined in FIG. 1. For example according to the present process as shown in FIG. 1, when the concentration of 2-methylglutaronitrile is 25% by weight then the concentrations of the water solution of the alkylamine must be 40% by weight and the concentration of the homogenizing solvent must be 35% by weight. FIG. 1 also indicates that at very low concentrations of 2-methylglutaronitrile or at very high concentrations of water the concentration of the homogenizing solvent may be zero.

The concentration of the primary alkylamine in the water solution may be any concentration of the alkylamine which is fully water soluble at the reaction conditions. This value will vary with the particular alkylamine used as a reactant. Generally for methylamine, the concentration is preferred to be 40% by weight, which is approximately the solubility of methylamine in water at room temperature and normal air pressure, but the concentration may be lower or slightly higher as conditions of temperature and pressure permit.

The presence of the homogenizing solvent in the reaction mixture provides more advantages than simply the conversion of a heretofore known batch process to a continuous process. The inventor has also found that by including the homogenizing solvent, the hydrogenation reaction proceeds at a slightly faster rate and with a surprising increase in 1,3 and 1,5-alkylmethylpiperidone-2 selectivity and a decrease in the formation of high boiling byproducts particularity bis-1,5-(alkylamido)-3-methylpentane. The present invention allows for a more favorable mix of products than is taught in the prior art. The favorable selectivity of the present invention is independent of the process being run as a batch or a continuous process. This selectivity is also independent of the type of continuous reactor which is used to run the present process.

Conventional commercial hydrogenation catalyst are useful in the process of the present invention. Such catalysts are Group VIII metals supported on substrates such as graphite, carbon, alumina, strontium or calcium carbonate, silicas, kieselgur, titania or zirconia. Palladium is the preferred Group VIII metal catalyst. The amount of catalyst employed will vary with the particular catalytic metal employed, the concentration of the metal on the substrate, the type of reactor and the reaction conditions.

A promoter such as Platinum, Rhenium, Tin, and Ruthenium or combinations thereof may be used with the catalyst. The concentration of the promoter may be from about 0.5% to about 5% by weight of the metal on the catalyst.

It is preferred to carry out the process at temperatures above about 150° C. and at a pressure above about 27 bars (400 psi).

Hydrogen should be present in the reactor in at least the stoichiometric amount. By stoichiometric is meant that the amount of hydrogen present is at least that amount sufficient to convert the nitrile to alkylamines and ammonia.

A continuous process according to the present invention may be run in continuous fixed bed reactor, a continuous stirred tank reactor, in a bubble column or an external loop reactor.

EXAMPLES

Example 1

This Example shows a continuous fixed bed hydrogenation of 2-methylglutaronitrile to 1,3 and 1,5-dimethylpiperidone-2 according to the present invention.

18.3 grams (60 cc) of 4×6 mash granular 2% by weight palladium on carbon hydrogenation catalyst was charged into a 36 inch (91.4 cm)×0.75 inch (1.9 cm) diameter Hastelloy C oil-jacketed, trickle bed reactor designed for continuous operation. The hydrogenated product recycle stream (product 1,3 and 1,5-dimethylpiperidone-2, other organics, a water solution of a primary alkylamine and amine) was used as the solvent diluent for this process. An aqueous methylamine solution, 40% amine by weight, was initially recycled over the hydrogenation catalyst at a rate of 100 ml per hour at 180° C. and 34 bars of hydrogen pressure.

Two streams were co-fed into the reactor. One stream was 2-methylglutaronitrile (99.5% by weight available from E. I. DuPont de Nemours and Company, Inc. Wilmington, Del.); the other was 40% by weight aqueous solution of methylamine. The feed rate was 7.4 ml/hr for the 2-methylglutaronitrile and 8.2 ml/hr for the aqueous amine. The recycle ratio was 6.4 to 1. The hydrogen flow rate used was 498 cc/min. The concentrations of a water solution of a primary alkylamine, 2-methylglutaronitrile and the 1,3 and 1,5-dimethylpiperidone-2 homogenizing solvent fell within the weight percents required by FIG. 1.

A product stream was removed at a rate of 15. cc/min from the reactor mixture and sent to a 2 liter stainless steel separator and held at 0.34 bar (5 psi) to allow the separation of hydrogen and ammonia from the product. Hydrogen and ammonia that separated from the product were vented to a nitrogen exit purge stream. The product take-off and reactant feed rates were such that the concentrations of a water solution of a primary alkylamine, 2-methylglutaronitrile and the 1,3 and 1,5-dimethylpiperidone-2 homogenizing solvent continued to fall within the weight percents required by FIG. 1.

Steady state operation was achieved in 24 hours.

After 45 hours of continuous operation, gas chromatographic analysis of the product showed the conversion of 2-methylglutaronitrile to be that 95%. The selectivity to 1,3 and 1,5-dimethylpiperidone-2 was 68%. The byproduct selectivity to 1,3-dimethyl-piperidine; bis-1,5-(methylamido)-3-methylpentane; 3- and 5-methylpiperidone-2 and other high boilers was 12%, 1%, 2.2% and 11%, respectively.

Example 2

This Example shows a continuous stirred tank reactor hydrogenation of 2-methylglutaronitrile to 1,3 and 1,5-dimethylpiperidone-2 according to the present invention.

100 ml of a 40% by weight solution of methylamine and 3 grams wet of a 50% by weight of catalyst having 5% by weight palladium on carbon powder were charges into a 300 cc stainless steel autoclave. The autoclave was equipped with a magadrive stirrer, a cooling coil, a thermocouple and a dip tube for product removal. After charging the autoclave, the reactor was sealed and purged with hydrogen three times.

The sealed, purged autoclave was heated to 180° C. and pressurized to 34 bars with hydrogen. Stirring was then started at 1000 rpms.

A stream of 99.5% by weight 2-methylglutaronitrile (available from E. I. DuPont de Nemours and Company, Inc. Wilmington, Del.) was fed into the autoclave at the rate of 10 ml/hour while a second stream of 40% aqueous methylamine was fed into the autoclave at a rate of 8.8 ml/hour. The hold-up time was 5 hours. The flow of hydrogen was 250 cc/minute.

A product stream was then drawn off at the rate of 17.6 ml/hour and sent to a 2 liter stainless steel pot as described in Example 1. As in Example 1, the concentrations of a water solution of a primary alkylamine, 2-methylglutaronitrile and the 1,3 and 1,5-dimethylpiperidone-2 homogenizing solvent in the initial reaction mixture fell within the weight percents required by FIG. 1.

Steady state operation was achieved in 40 hours.

After 161 hours running time with product take-off, the pressure in the autoclave was raised to 54.4 bars (800 psi).

As in Example 1, as product was taken-off, the rate of product take-off and the rate of reactant feed was balanced so that the concentrations of a water solution of a primary alkylamine, 2-methylglutaronitrile and the 1,3 and 1,5-dimethylpiperidone-2 homogenizing solvent continued to fall within the weight percents required by FIG. 1.

After 304 hours on stream, gas chromatographic analysis of the product showed the conversion of 2-methylglutaronitrile to be that 92%. The selectivity to 1,3 and 1,5-dimethylpiperidone-2 was 68.7%. The byproduct selectivity to 1,3-dimethylpiperidine; bis-1,5-(methylamido)-3-methylpentane; 3- and 5-methylpiperidone-2 and other high boilers was 9.5%, 3.5%, 9.0% and 13.3%, respectively.

Example 3

This examples shows a batch hydrogenation of 2-methylglutaronitrile to 1,3- and 1,5-dimethylpiperidone-2 employing a homogenizing solvent of N-methylpyrrolidone.

Into a 300 ml stainless steel autoclave was charged 38 grams of 2-methylglutaronitrile, 49 ml of a 40% aqueous methylamine solution, 2.3 grams of water, 60 g N-methylpyrrolidone and 1.5 g of a 5% palladium on carbon catalyst (4.0% catalyst loading based on 2-methylglutaronitrile).

This mixture formed a homogeneous solution of the three components.

The reactor was closed and purged twice with nitrogen and hydrogen and then pressured to 100 psig with hydrogen at room temperature.

The mass was heated to 180° C. and pressured to 34 bars (500 psig) with hydrogen and the agitator turned on to 1100 rpm.

Hydrogen uptake was monitored by a transducer connected to a recorder. The reduction required 120 minutes. After that time no additional hydrogen uptake was observed.

GC analysis of the reaction mass showed complete conversion of 2-methylglutaronitrile. The selectivity to 1,3- and 1,5-dimethylpiperidone-2 was 56.7%. The byproduct selectivity to 1,3-dimethylpiperidine; bis-1,5-(methylamido)-3- methylpentane; 3- and 5-methylpiperidone-2 and other high boilers was 7%, 2.4%, 1.7% and 29.9%, respectively.

Example 4

This example shows the hydrogenation of 2-methylglutaronitrile to 1,3- and 1,5-dimethylpiperidone-2 in the absence of a homogenizing solvent.

Into a 300 ml stainless steel autoclave equipped with a stirrer was charged 60 g 2-methylglutaronitrile, 80.3 ml of a 37.8% aqueous methylamine solution and 4.8 g of a 5% palladium on carbon catalyst (4.0% catalyst loading based on 2-methylglutaronitrile).

This mixture contained two separate liquid phases.

The reactor was closed and purged twice with nitrogen and hydrogen and then pressured to 100 psig with hydrogen at room temperature. The mass was heated to 180° C. and pressured to 34 bars (500 psig) with hydrogen and the agitator turned on to 1100 rpm. Hydrogen uptake was monitored by a transducer connected to a recorder.

The reduction required 240 minutes after which time no additional hydrogen uptake was observed.

GC analysis of the reaction mass showed complete conversion of 2-methylglutaronitrile. The selectivity to 1,3- and 1,5-dimethylpiperidone-2 was 43.5%. The byproduct selectivity to 1,3-dimethylpiperidine; bis-1,5-(methylamido)-3-methylpentane; 3- and 5-methylpiperidone-2 and other high boilers was 1.0%, 42.1%, 2.0% and 15%, respectively.

Table I below shows a comparison of selectivity of the prior art and the present invention. Reaction conditions are shown in the Table. The reaction conditions of the present invention are shown in entries 9 to 12.

TABLE 1

| Catalyst | Wt. % | Temp., °C. | Press psig | Solvent | mol. wt 172 % sel | DPMD % sel | No |
|---|---|---|---|---|---|---|---|
| 5% Pd/C | 4.0 | 180 | 500 | none | 32.1 | 53.4 | 1 |
| 5% Pd/C | 0.5 | 180 | 500 | none | 42.1 | 43.5 | 2 |
| 4.5% Pd/ 0.5% Pt/C | 3.2 | 200 | 800 | none | 31.8 | 43.6 | 3 |
| 5% Pd/C | 2.8 | 180 | 800 | none | 17.0 | 55.5 | 4 |
| 5% Pd/C | 2.0 | 180 | 1500 | none | 30.5 | 52.7 | 5 |
| 5% Pd/C | 4.0 | 180 | 1000 | none | 26.9 | 57.3 | 6 |
| 5% Pd/C | 4.0 | 180 | 2000 | none | 20.2 | 54.6 | 7 |
| 4.5% Pd/ 0.5% Pt/C | 6.4 | 200 | 800 | none | 33.5 | 49.6 | 8 |
| 5% Pd/C | 3.2 | 180 | 500 | NMP | 1.5 | 54.7 | 9 |
| 4.5% Pd/ 0.5% Pt/C | 4.3 | 190 | 500 | NMP | 7.5 | 69.6 | 10 |
| 4.5% Pd/ 0.5% Pt/C | 4.7 | 200 | 800 | NMP | 4.8 | 53.4 | 11 |
| 4.5% Pd/ 0.5% Pt/C | 3.2 | 200 | 800 | NMP | 6.7 | 58.5 | 12 |

In the Table:
MGN conversions are > 95%; NMP stands for n-methylpyrrolidone; DMPD stands for dimethylpiperidone-2;
mol wt 172 Stands for the byproduct bis-1,5-(methylamido)-3-methylpentane since this is the molecular weight of the byproduct.

Figure 2:
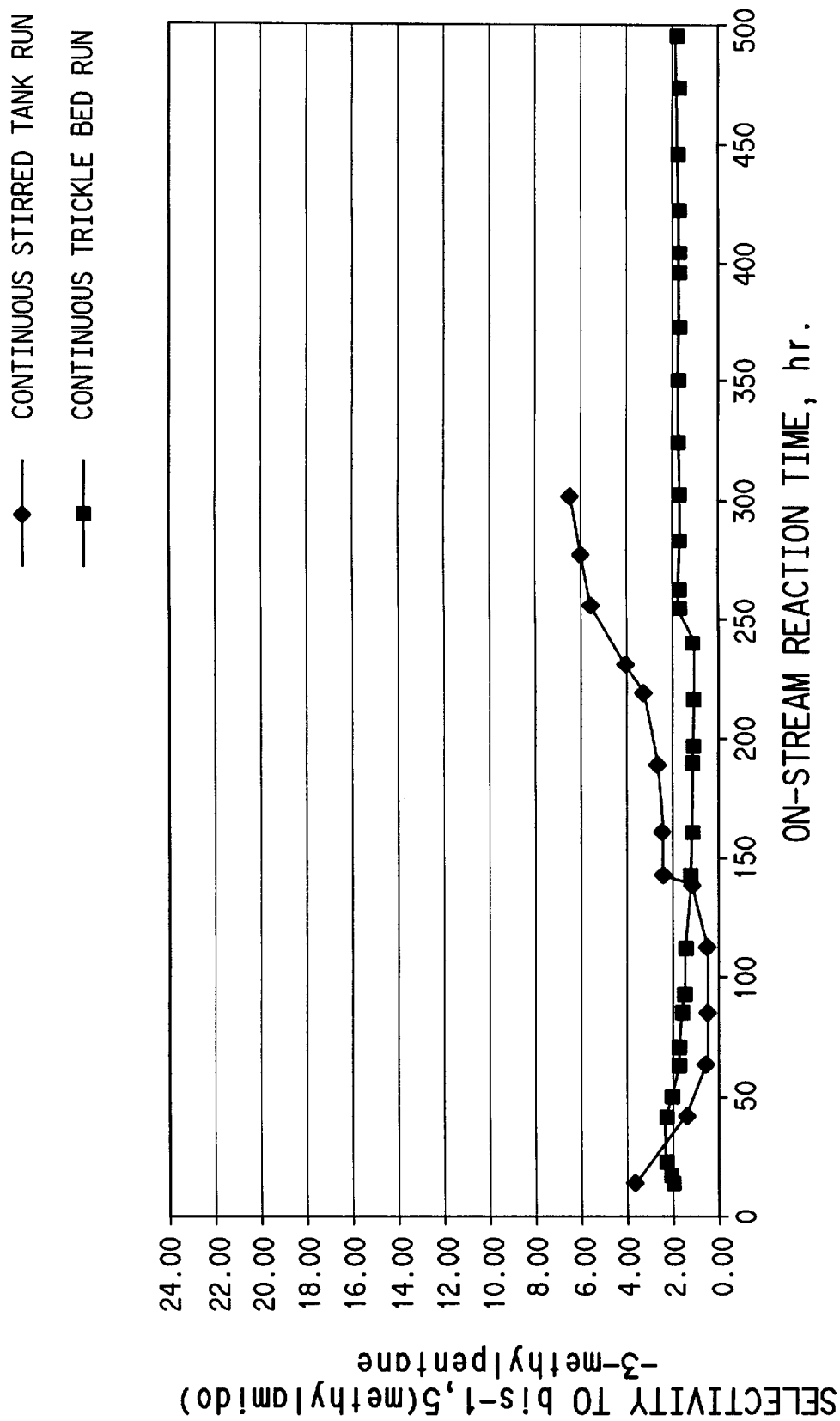
FIG. 2 shows the selectivities of bis-1,5-(methylamido)-3-methylpentane in both continuous stirred tank (CSTR) and continuous trickle bed operation over 200 hours of operation at MGN conversions of 90%.

FIG. 2 shows selectivities of bis-1,5-(methylamido)-3-methylpentane in both continuous stirred tank (CSTR) and continuous trickle 15 bed operation over 200 hours of operation at MGN conversions of 90%. For the continuous processes which are the process of the present invention, the selectivity is low to bis-1,5-(methylamido)-3-methylpentane compared to batch operation of the prior art which requires no homogenizing solvent.

What is claimed is:

1. A continuous process for the preparation of 1-alkyl-3-methylpiperidone-2 and 1-alkyl-5-methylpiperidone-2 from hydrogen and a single phase, liquid reaction mixture of 2-methylglutaronitrile, a water solution of a primary alkylamine which contains from 1 to 18 carbons, a homogenizing solvent in the presence of a hydrogenation catalyst wherein the selectivity of the process to bis-1,5-(methylamido)-3-methylpentane is less than 8%, comprising the steps of:

(a) contacting the hydrogenation catalyst in a reaction vessel with the single phase liquid reaction mixture wherein the weight percents of the homogenizing solvent, the water solution of the primary alkylamine, and 2-methylglutaronitrile based on the total weight of the single phase liquid reaction mixture are within the region of FIG. 1 bounded by the lines AB, BC, and AC;

(b) feeding into the reaction vessel one or more reactant streams containing 2-methylglutaronitrile, the water solution of the alkylamine and hydrogen;

(c) heating the reaction mixture to a temperature above about 150° C. at a hydrogen pressure above about 27 bars (400 psi); and (d) withdrawing a product stream from the reaction mixture containing 1-alkyl-3-methylpiperidone-2 and 1-alkyl-5-methylpiperidone-2 while at the same time continuing to feed into the reaction vessel the reactant streams of step (b) in such a way as to maintain the weight percent of the homogenizing solvent, the water solution of the alkylamine, and 2-methylglutaronitrile based on the total weight of the single phase liquid reaction mixture within the region of FIG. 1 bounded by the lines AB, BC, and AC.

2. The process of claim 1 wherein the homogenizing solvent is selected from the group consisting of dioxane, N-methylpyrrolidone, 1,3-dimethylpiperidone-2, 1,5-dimethylpiperidone-2, a mixture of 1,3 and 1,5-dimethylpiperidone-2 and N-methyl or higher N-alkyl lactams having properties of water miscibility and solubility for the alkylamines and 2-methylglutaronitrile.

3. The process of claim 1 wherein the primary alkylamine is methylamine and in which the product are 1,3-dimethylpiperidone-2, 1,5-dimethylpiperidone-2.

4. An improved batch process for the preparation of 1-alkyl-3-methylpiperidone-2 and 1-alkyl-5-methylpiperidone-2 from 2-methylglutaronitrile, a water solution of a primary alkylamine which has from 1 to 18 carbons, and hydrogen and in the presence of a hydrogenation catalyst at a pressure of above about 27 bars (400 psi) and a temperature of above about 150° C., the improvement comprising mixing with the hydrogenation catalyst a single phase liquid mixture of 2-methylglutaronitrile, the water solution of the primary alkylamine and a homogenizing solvent such that the concentrations of each of these components as weight percents of the total liquid phase fall within the region of FIG. 1 bounded by the lines AB, BC and AC and wherein the selectivity of the process to bis-1,5-(methylamido)-3-methylpentane is less than 8%.

5. The process of claim 4 wherein the homogenizing solvent is selected from the group consisting of dioxane, N-methylpyrrolidone, 1,3-dimethylpiperidone-2, 1,5-dimethylpiperidone-2, a mixture of 1,3 and 1,5-dimethylpiperidone-2 and N-methyl or higher N-alkyl lactams having properties of a water solution of a primary alkylamine miscibility and solubility for primary alkylamines and 2-methylglutaronitrile.

6. The process of claim 4 wherein the primary alkylamine is methylamine and in which the product are 1,3-dimethylpiperidone-2, 1,5-dimethylpiperidone-2.

* * * * *